(12) United States Patent
Evans et al.

(10) Patent No.: US 6,291,378 B1
(45) Date of Patent: Sep. 18, 2001

(54) DENTAL RESTORATIONS

(75) Inventors: Philip Anthony Evans, Bradford; Paul Harrison, Ilkley, both of (GB)

(73) Assignee: Techceram Limited, West Yorkshire (GB)

(*) Notice: Subject to any disclaimer, the term of this patent is extended or adjusted under 35 U.S.C. 154(b) by 0 days.

(21) Appl. No.: 09/468,395

(22) Filed: Dec. 20, 1999

(51) Int. Cl.⁷ .......................... C04B 35/565; B28B 7/34
(52) U.S. Cl. .................. 501/88; 501/89; 501/111; 501/133; 106/35; 106/38.3; 106/38.9; 433/215
(58) Field of Search .................. 501/88, 89, 111, 501/133; 406/35, 38.3, 38.9; 433/215

(56) References Cited

U.S. PATENT DOCUMENTS 5,013,363   5/1991   Hakamatsuka et al. .
5,298,200   3/1994   Kubo et al. .

FOREIGN PATENT DOCUMENTS 4030542   3/1992   (DE) .

*Primary Examiner*—Karl Group
(74) *Attorney, Agent, or Firm*—Klauber & Jackson

(57) ABSTRACT

The invention provides a refractory material for use in the manufacture of dental restorations, the refractory material comprising essentially of an admixture of Silica, Silicon Carbide, Magnesium Oxide, Mono Ammonium Phosphate, and Zircon or Aluminium Oxide in predetermined proportions by weight. The material is formed as an homogenous powder and mixed with a colloidal silica based solution to form a creamy mixture suitable for casting into a silicone based impression of a prepared tooth so as to form a refractory model of said tooth. The homogenous powder may be stored in moisture resistant material until required to be mixed with said colloidal silica based solution.

8 Claims, 1 Drawing Sheet

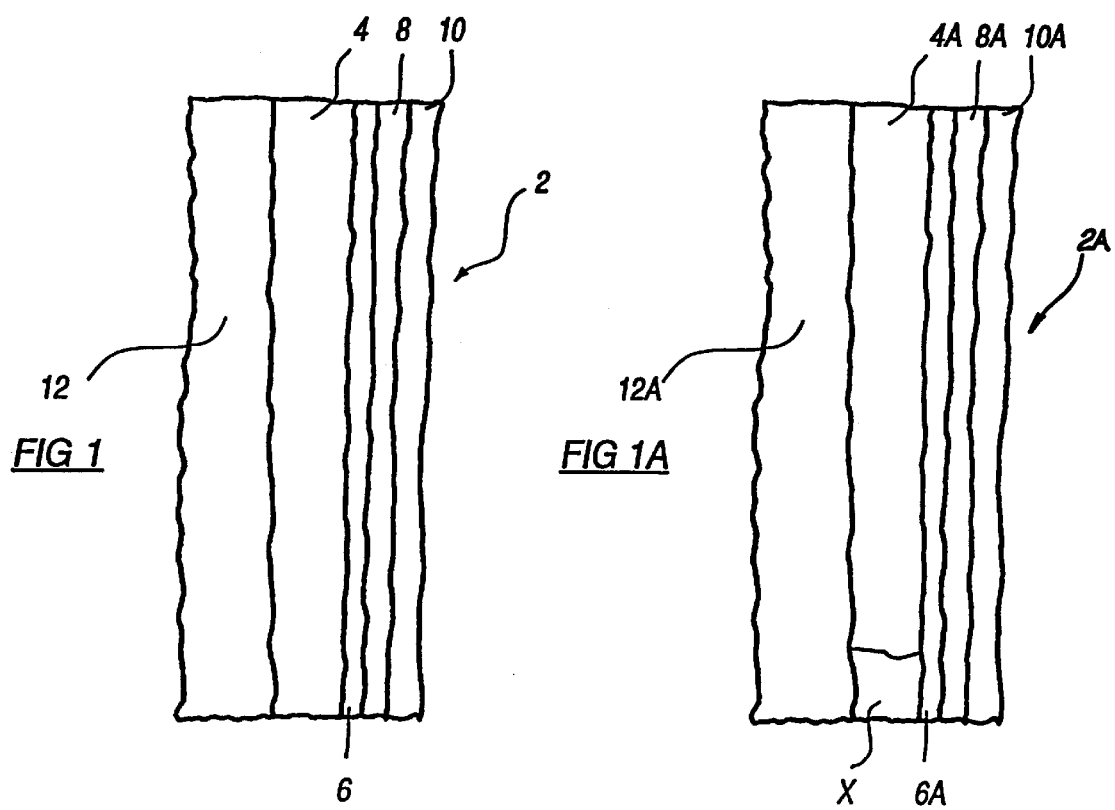
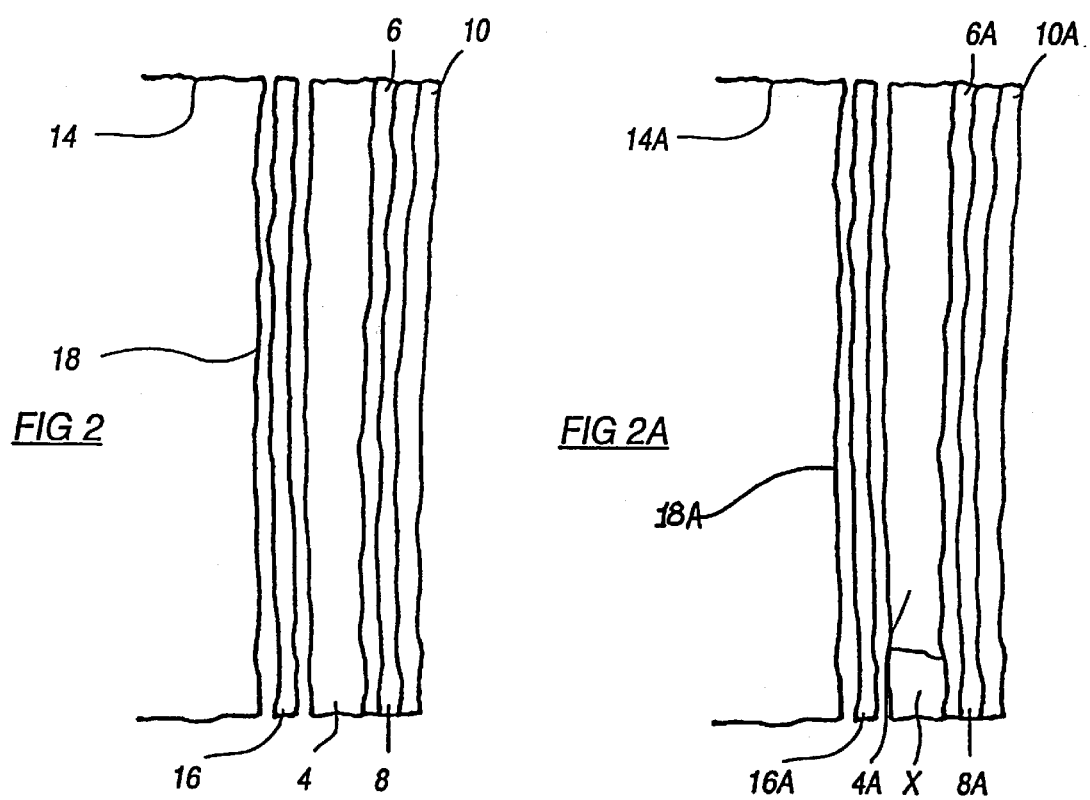

DENTAL RESTORATIONS

This invention relates to a material for use in the fabrication of full or partial dental restorations, including veneers, crowns, inlays, on lays, and bridge structures, hereinafter referred to as dental restorations.

The invention utilises the technique of flame spraying to produce a relatively dense basal layer of a technical ceramic based material which firstly acts a permanent form upon which porcelain can be applied in order to yield ultimate aesthetics of the restoration, and which secondly serves to strengthen the restoration and provide a means for bonding the restoration to a prepared tooth in which the contribution made by the mechanical bonding mechanism is enhanced.

According to the present invention there is provided a high thermal conductivity refractory material for use in the manufacture of dental restorations, said refractory material comprising essentially of an admixture of Silica, Silicon Carbide, Magnesium Oxide, Mono Ammonium Phosphate, and Zircon or Aluminium Oxide, in predetermined proportions by weight.

The refractory material will preferably be formed as an homogenous powder and sealed in moisture resistant material and subsequently preferably mixed with a colloidal silica based solution.

Preferably, the homogenous powder and colloidal silica based solution is formed into a creamy mixture, preferably by means of a vacuum mixer, prior to being cast into a silicone based impression of a prepared tooth so as to form a refractory model of said tooth.

The silica ($SiO_2$) content is preferably in the form of fused silica, quartz, cristobalite, or tridymite

BRIEF DESCRIPTION OF DRAWINGS

In order that the invention may be more readily understood, an embodiment thereof will now be described, by way of example, reference being made to the accompanying drawings, in which:

FIGS. 1 and 1a are cross-sectional elevations of dental restorations incorporating a refractory model composed of the material of the invention; and FIGS. 2 and 2a are cross-sectional elevations of the dental restorations of FIGS. 1 and 1a with the refractory models removed and shown positioned relative to a natural tooth.

Referring to the drawings, and firstly to FIG. 1, there is shown a section of a dental restoration indicated generally by reference numeral 2. The dental restoration comprises a base layer 4 of technical ceramic material such as Alumina, Zirconia, or Titania, or combinations thereof, and subsequent layers 6, 8, and 10 of dental porcelains which are applied to the base layer 4 to enhance the aesthetics of the restiration.

In the formation of the restoration, there is firstly formed a model 12 of a prepared tooth in a refractory material which is an 'active' eliminable material and which comprises essentially of an admixture of Silica, Silicon Carbide, Magnesium Oxide, Mono Ammonium Phosphate, and Zircon or Aluminium Oxide, a typical composition being as follows:

| Material | Weight % |
| --- | --- |
| Silica ($SiO_2$) | 20–88 |
| Silicon Carbide (SiC) | 2–40 |
| Zircon ($ZrSiO_4$) | 0–20 |
| Aluminium Oxide ($Al_2O_3$) | 0–20 |
| Magnesium Oxide (MgO) | 5–20 |
| Mono Ammonium Phosphate | 5–20 |

The above materials are mixed to form a homogenous powder and then sealed in moisture resistant material. The homogenous powder, when required, is then mixed with a colloidal silica based solution in a vacuum mixer to form a creamy mixture which is poured into a silicone based impression of the prepared tooth and allowed to set, to yield and actively obtain the desired set expansion and green strength. The silica ($SiO_2$) content can be varied in nature, i.e. fused silica, quartz, cristobalite or tridymite in order to alter the coefficient of thermal expansion of the ultimate refractory material to suit use with low or high coefficient of thermal expansion dental porcelains. The addition of Silicon Carbide to the refractory material increases the thermal conductivity. Variation in the formulation and in the type and concentration of the colloidal silica based solution will alter the set expansion and green strength. Variation in the particle size of the constituents will affect the density and smoothness of the final refractory.

After formation of the model 12 of refractory material, the model 12 is subjected to burn out and optionally a hardening heat treatment in a furnace at temperatures in the range 1000–1150° C. which,.due to the subsequent associated shrinkage of the model,ensures that a net overall expansion to shrinkage may be designed in for different applications, i.e. for different restorations. For example, in the case of a refractory model for forming base layers for crown type applications, a net overall positive expansion is designed in such that no 'over' layer has to be applied to the refractory model 12 prior to the formation of the base layer as is the case, for example, in prior proposals.

The refractory model is cooled and during such cooling, i.e. simultaneously therewith, the base layer 4 is applied directly to the said model 12 by flame spraying techniques which include plasma spraying and detonation gun methods of application, the base layer then being sintered at a high temperature. The layers 6, 8, and 10 of dental porcelains are then applied to said base layer.

The base layer 4 is sintered either whilst it is still on the refractory model 12—or alternatively it may be sintered following removal of the model 12—by, for example, microblasting with glass beads. Similarly, the layers 6, 8, and 10 of dental porcelains may be applied to the base layer either whilst the base layer is still on the refractory model 12 or alternatively after removal of the refractory model 12.

Once the base layer has been sintered—either on or off the refractory model 12, and in either case the model 12 removed—the base layer 4 may be trimmed using a hand piece and diamond burr.

Referring now to FIG. 1a—where like parts are given the same reference numerals as in FIG. 1 but with the suffix 'A'—the base layer 4A may then be re-fitted to another refractory model 12A (formed in the same manner as described above, and then heat treated) and the layers 6A, 8A, and 10A of dental porcelains applied to complete the restoration in the normal manner. In FIG. 1a, layer X represents a marginal material 'cerabond' which yields extremely accurate margins.

Referring now to FIG. 2, the dental restoration—with the refractory model 12 removed—is shown applied to a natural tooth 14 through the intermediary of a layer 16 of bonding agent. Prior to the application of the dental restoration to the natural tooth 14, treatment of the tooth surface 18 may be necessary (depending upon the type of bonding material used) such treatment involving the use of the phosphoric acid etching technique. FIG. 2a shows the restoration of FIG. 1a applied to a natural tooth 14A, and therefore like parts have been given the same reference numerals as in FIG. 2 but with the suffix 'A'.

The flame spray process used in the method of the invention utilises a free flowing powder or liquid which incorporates a technical ceramic based material such as Alumina, Zirconia, or Titania, or combinations thereof. The free flowing powder or liquid is introduced into the flame/plasma whereupon it is given kinetic energy and thermal energy and directed at the target, i.e. the model 12 of refractory material which will have been pre-formed by the afire-mentioned process.

Swift passes are made so as to deposit the technical ceramic based material onto the model 12 of refractory material in a series of successive layers, this action serving to facilitate the fabrication of a relatively dense microstructure.

Small amounts of silicate based materials may be added to the pre-cursor feed materials to facilitate the production of a fully dense technical ceramic based material layer 4. Alternatively, the silicate based material may be added once the base layer has been formed.

It should be noted that, dependent upon the type of technical ceramic based material used and the end result that is required, post-flame spray heat treatment of the base layer is necessary prior to the application of the layers of dental porcelain, not only to fully densify the base layer 4 but also to homogenise alloying additions or phases present and to enhance the optical properties of the base layer. It should be noted that it is only after trimming that base layer 4 becomes base layer 4A.

Due to the nature of the microstructure produced following flame spraying, any small amount of remaining shrinkage of the layer is promoted throughout the depth of the layer, thus not affecting the fit of the final restoration to the tooth.

Utilising the optimum conditions outlined, a base layer approaching theoretical density can be produced. The finished thickness of the base layer will be dependent upon which type of restoration is being manufactured and may vary from a single particulate layer in the order of 1 micro-meter to a substantial layer in the order of 3 millimeters.

The flame spray process used to produce the base layer is a 'direct' technique—utilising the refractory technique and following the formation of the base layer, conventional techniques are used for the application of the layer(s) of dental porcelain. The first layer of dental porcelain must have a co-efficient of thermal expansion which is matched to, or preferably lower than that of the technical ceramic based material base layer. A porcelain having this slightly lower co-efficient of thermal expansion will be placed into slight compression upon cooling, thus yielding a dental restoration with optimum strength properties and aesthetics.

A dental restoration incorporating a base layer produced in accordance with the invention—and formed on a model of refractory material as defined and as referred to above—has excellent shape retention, since the normally large shrinkages (typically 15 to 20%) experienced on sintering a technical ceramic formed by casting, die pressing or slurry build-up techniques are greatly reduced or overcome. The strength of the dental restoration produced is greater than similar dental restorations which are manufactured from porcelain based materials.

The formation of the model of refractory material—of high thermal conductivity and matched thermal expansion—allows the base layer to be flame sprayed directly onto the cooled refractory model without producing cracks in the base layer, unlike all commercially available phosphate bonded dental refractories (having lower thermal conductivity) which have been found to be unsuitable for direct spraying, yielding cracks in base layers and proving difficult, if not impossible, to blast out following spraying or further heat treatment. Thus more consistent, crack-free technical ceramic base layers can be produced.

It is thus the combination of a refractory of high thermal conductivity (incorporating SiC) with the cooling effect which confers the beneficial properties on the base layer with respect to crack-free properties, unlike a previosly proposed manfacturing process which was limited in time of processing so as not to overheat the model or support. It is the combination of the formulation of the refractory with the formulation of the colloidal silica which confers the beneficial 'active' eliminable properties on the refractory, thereby negating the need for an 'over' layer, thus resulting in accurate fitting base layers.

The model of refractory material allows flame sprayed base layers to be sintered at high temperatures (1000° C. to 1200° C.) on the refractory material if required, and the refractory to be removed by microblasting with glass beads in the normal manner either directly following spraying or following sintering, or following porcelain build-up. Alternatively, the base layer may be sintered off the refractory model. All commercially available phosphate bonded dental refractories have been found to be too hard after such processing and cannot be removed by micro-blasting. Additionally, use of cooling is not as effective due to the low thermal conductivity of commercially available dental refractories.

The technique of removing the refractory model, sintering and trimming the base layer, and re-fitting the base layer to another refractory model prior to the application of the layer(s) of porcelains, has the advantage that the applied layer(s) of porcelains are supported during firing at the marginal area and hence an accurate marginal fit may be produced in fully fired, dense porcelain layer X which yields optimal biocompatability with gingival tissue. Normally, base layers of any type—whether ceramic or metal—have margins which are fired unsupported and thus require special powders or liquids or combinations of the two.

The refractory model may have a net overall zero to small positive expansion actively designed in to yield extremely accurate margins. Further, this type of refractory is optionally hardened via a heat treatment cycle following burn out.

The formation of the refractory model 12A upon which a trimmed sintered base layer is fitted and subsequent layer(s) of porcelain applied to complete the final restoration is innovative.

There are various model systems including but not limited to Pindex, E-Z tray, Accutrack type, Single cast type etc, for which a refractory model can be produced to substitute into the prepared master model site.

It should be noted however that whichever model system is used, the fitting of a trimmed, formed (sintered) base layer to the refractory model, prior to the addition of layer(s) of porcelain is novel, and yields marginal areas of exact fit which are excellent in aesthetics and gingival biocompatability.

Normally, porcelains, when used alone for veneer, inlay, onlay, and bridge type applications, need to be fired on the refractory. With commercially available low thermal conductivity refractory materials, different firing conditions are required (often higher temperature), but due to the higher thermal conductivity of the refractory material according to the invention, the same or similar conditions and materials can be used for firing in dental furnaces on the model of refractory material.

In addition, and with special reference to low fusing porcelains, the porcelains may be fired reproducibly at any point in the furnace muffle, i.e. either centrally or radially adjacent to the heating elements.

Finally, by a combination of materials and process variations, satisfactory aesthetics can be produced which take account of hue, value, chroma, translucency, shape, outline form, contour, proportion and soft tissue harmony with the oral cavity.

What is claimed is:

1. A refractory material for use in the manufacture of a dental restoration consisting essentially of an admixture of Silica, Silicon Carbide, Magnesium Oxide, and Mono Ammonium Phosphate in predetermined proportions by weight, and optionally Zircon or Aluminium Oxide in predetermined proportions by weight.

2. A refactory material according to claim 1, wherein said proportions are:

| Silica | 20–88% | Silicon Carbide | 2–40% |
|---|---|---|---|
| Magnesium Oxide | 5–20% | Mono Ammonium Phosphate | 5–20% |
| Zircon | 0–20% | Aluminium Oxide | 0–20%. |

3. A refractory material according to claim 1, wherein the Silica is in the form of fused silica, quartz, cristobalite, or tridymite.

4. A refractory material according to claim 1, wherein said refractory material is formed as a homogenous powder and mixed the colloidal silica based solution.

5. A refractory material according to claim 4, wherein said homogenous powder is sealed in moisture resistant material until required to be mixed with said colloidal silica based solution.

6. A refractory material according to claim 4, wherein the homogenous powder and colloidal silica based solution is formed into a creamy mixture prior to being cast into a silicone based impression of a prepared tooth so as to form a refractory model of said tooth.

7. A refractory model for use in the manufacture of a dental restoration, said refractory model being composed of a refractory material according to claim 1.

8. A dental restoration including a refractory model according to claim 7.

* * * * *